United States Patent [19]

Brown

[11] 4,405,598
[45] Sep. 20, 1983

[54] COMPOSITION FOR TREATING ASTHMA

[75] Inventor: Kenneth Brown, East Leake, England

[73] Assignee: Fisons, Limited, Ipswich, England

[21] Appl. No.: 224,747

[22] Filed: Jan. 13, 1981

Related U.S. Application Data

[63] Continuation-in-part of Ser. No. 56,470, Jul. 11, 1979, abandoned, which is a continuation of Ser. No. 868,474, Jan. 11, 1978, abandoned, which is a continuation-in-part of Ser. No. 761,445, Jan. 21, 1977, abandoned, and a continuation-in-part of Ser. No. 89,033, Oct. 29, 1979, abandoned, which is a continuation of Ser. No. 920,174, Jun. 29, 1978, abandoned, which is a continuation-in-part of Ser. No. 868,474, Jan. 11, 1978, abandoned.

[51] Int. Cl.$^3$ ............................................. A61K 31/35
[52] U.S. Cl. ...................................... 424/45; 424/283
[58] Field of Search ................................ 424/45, 283

[56] References Cited

U.S. PATENT DOCUMENTS 3,282,791 11/1966 Macek ..................................... 424/45
3,560,607 2/1971 Hartley ................................... 424/46
3,897,779 8/1975 Hansen ................................... 128/266

OTHER PUBLICATIONS

Physicians Desk Reference, (PDR), 30th Ed., pp. 805–806.

Merck Index–9th Ed., 1976.
Remington's Pharmaceutical Chemistry, 13th Ed., pp. 659–662.

*Primary Examiner*—Leonard Schenkman
*Attorney, Agent, or Firm*—Merriam, Marshall & Bicknell

[57] ABSTRACT

There is described a method of treatment of asthma which comprises administration to an asthmatic patient of an effective amount of an inhalation composition consisting essentially of a dispersion or suspension of from 0.2 to 2.0% disodium cromoglycate of mass median diameter 0.01 to 10 microns, from 0.15 to 2.0% by weight of a sorbitan or sorbitol ester surfactant and a propellant mixture comprising dichlorodifluoromethane and 1,2-dichloro-1,1,2,2-tetrafluoroethane, the ratio of dichlorodifluoromethane to 1,2-dichloro-1,1,2,2-tetrafluoroethane, in said mixture being in the range from 2:1 to 1:1 by weight, the disodium cromoglycate used in the formulation containing from 0.05 to 1% w/w of water and the total formulation containing less than 0.1% w/w of water and having a vapor pressure in the range 35 to 70 pounds per square inch gauge.

There is also described disodium cromoglycate having a mass median diameter of less than 20 microns, more preferably in the range 0.01 to 10 microns, and most preferably at least 50% by weight of the particles having a diameter of 2 to 5 microns and containing less than 1% by weight of water.

3 Claims, No Drawings

COMPOSITION FOR TREATING ASTHMA

This is a continuation in part of application Ser. No. 56,470 filed July 11, 1979, now abandoned which in turn is a continuation of application Ser. No. 868,474, filed Jan. 11, 1978, now abandoned which in turn is a continuation-in-part of application Ser. No. 761,445, filed Jan. 21, 1977, now abandoned, and is also a continuation-in-part of application Ser. No. 89,033 filed Oct. 29, 1979, now abandoned which is a continuation of Ser. No. 920,174, filed June 29, 1978, now abandoned which in turn is a continuation-in-part of application Ser. No. 868,474, filed Jan. 11, 1978 now abandoned.

This invention relates to disodium cromoglycate in a novel form and to a novel pharmaceutical formulation containing disodium cromoglycate.

Disodium cromoglycate has since 1967 been sold under the Registered Trade Mark 'Intal' in admixture with lactose as a powder for the inhalation therapy of asthma. For such use the disodium cromoglycate normally contains between about 8 and 10% by weight of water; disodium cromoglycate containing this proportion of water being stable in contact with air of normally encountered humidities.

We have now found that disodium cromoglycate containing smaller proportions of water, while technically very difficult to produce and handle, has considerable advantages in the production of aerosol formulations of the drug.

The powder formulation 'Intal' is sold in a hard gelatine capsule containing 20 mg of drug and 20 mg of lactose, which in use, is placed in a special inhalation device (sold under the Registered Trade Mark 'Spinhaler') where the capsule is pierced. The user then inhales through the device causing the capsule to rotate and vibrate and the mixture of the disodium cromoglycate and the lactose to be dispersed into the inhaled air stream. In this operation the piercing of the capsule is a critical step and it has been found that the water content of the gelatin is a critical factor in satisfactory piercing. If the water content of the gelatin is too low the capsule will shatter and the patient is then liable to inhale large fragments of gelatin. It has been found that shattering begins to occur at 11% w/w moisture in the gelatin. The normal gelatin shell of an 'Intal' capsule contains about 13.5% w/w moisture, and the 20 mg of normal disodium cromoglycate in the 'Intal' contains about 9% w/w moisture. Under these conditions the moisture in the gelatin and in the disodium cromoglycate are in equilibrium. Should the hydrated disodium cromoglycate be replaced by anhydrous material the anhydrous material would extract about 2 mg of water from the gelatin shell (the lactose remaining unaffected), bringing the water in the gelatin shell well below the 11% shattering limit. Thus use of anhydrous disodium cromoglycate in an 'Intal' type of formulation would be disastrous.

As stated above disodium cromoglycate normally contains about 9% w/w water and material of this degree of hydration can be easily handled under conditions of humidity usually found in a pharmaceutical manufacturing area. Use of disodium cromoglycate containing less than 9% w/w would be very difficult and would involve (i) a separate drying step, and (ii) the use of an environment of a controlled low humidity, and is thus most unattractive to a manufacturing pharmacist.

It has also for many years been known to administer medicaments, e.g. steroids, by means of pressurised areosol formulations (see for example U.S. Pat. No. 3,282,791). Such aerosols can be of a wide variety of types and usually involve solutions (for soluble substances), suspensions for insoluble materials, emulsions or semi-solid preparations. However prior to the present invention no satisfactory aerosol formulation of the water soluble disodium cromoglycate has been available because of the very considerable difficulties caused, inter alia by the particular, and unusual, properties (e.g. unlike other drugs it can incorporate water in its crystal lattice in virtually any proportion and is extremely hygroscopic) of disodium cromoglycate.

The conventional aerosol formulations for inhalation usually contain propellant 11 (trichloromonofluoromethane). However propellant 11 has been found to have undesirable environmental and toxic side effects, but it has in the past not, in practice, been possible to avoid the use of this propellant when it has been necessary to include the most favoured surfactants for inhalation.

These most favoured surfactants include various esters, notably sorbitan esters, e.g. sorbitan oleates such as sorbitan sesquioleate ('Arlacel C'), sorbitan mono-oleate ('Span 80'), sorbitan trioleate ('Span 85'), sorbitan monolaurate, polyoxyethylene sorbitol pentaoleate and polyoxyethylene sorbitol tetraoleate.

The common practice in pressure pack manufacture has been to make a so-called 'concentrate' or 'nucleus suspension' of the medicament, and one of the above surfactants in either propellant 11 or propellant 114 (1,2-dichloro-1,1,2,2-tetrafluoroethane). These concentrates may, because of the relatively high boiling point of the propellants, be handled at, or just below, room temperature. It has however been found that the surfactants mentioned above are extremely difficult to disperse in propellant 114 and these surfactants have therefore, in practice, been dispersed in propellant 11. Other propellants of lower boiling point have not been used because the surfactants would not dissolve in these other propellants at the low temperatures involved and furthermore would be solid at these low temperatures.

We have now found that the multifarious problems associated with the formulation of disodium cromoglycate as an aerosol can be overcome by a surprising and very specific combination of factors. Furthermore we have found that by use of such a formulation the effective dosage of disodium cromoglycate may be reduced from the 20 mg conventionally used in the 'Intal' capsule to 4 mg or below.

Thus according to the invention we provide a dispersion or suspension of a sorbitan or sorbitol ester and disodium cromoglycate in a mixture of propellant 12 and propellant 114, the dispersion or suspension containing no propellant 11, and preferably containing no other propellants whatsoever, the total formulation containing less than 1.0%, preferably less than 0.5%, more preferably less than 0.2% and most preferably less than 0.1% by weight of water.

Propellant 12 which has a vapour pressure of about 70 pounds per square inch gauge and propellant 114 which has a vapour pressure of about 12 pounds per square inch gauge at 70° F., may be mixed in various proportions to form a propellant having a desired intermediate vapour pressure.

It is desirable that the vapour pressure of the propellant employed be between 35 and 70, and preferably between 50 and 65 pounds per square inch gauge at 70° F. Such pressures are useable safely with metal containers.

We prefer the ratio of propellant 12 to propellant 114 in the mixture to be in the range 2 to 1:1, and preferably about 1.5:1 by weight; i.e. we prefer an excess of propellant 12 over propellant 114.

We prefer the dispersion or suspension of the surfactant in the final mixture of propellants 12 and 114 to contain from 0.15 to 2.0%, preferably 0.2 to 1.2% by weight of the sorbitan or sorbitol ester. We also prefer such dispersions or suspensions to contain from 0.05 to 2.0%, and preferably from 0.2 to 2.0%, by weight of disodium cromoglycate.

Dispersions of from 0.2 to 2 parts by weight of sorbitan ester in a mixture of from 50 to 70 parts by weight of propellant 12 and from 50 to 30 parts by weight of propellant 114 are stable for at least 16 hours at a temperature of −60° C.

We particularly prefer dispersions in which the surfactant is a sorbitan ester, e.g. sorbitan trioleate ('Span 85').

The dispersion may be made by adding the sorbitan or sorbitol ester to the propellant 12 (or to a mixture of propellants 12 and 114) at a temperature of below about −30° C., e.g. at −40° C., using a high dispersion mixer. The dispersion at this stage preferably comprises less than 4.0%, e.g. from 0.2 to 2.0%, w/w of the sorbitan or sorbitol ester. In making the initial suspension the surfactant solidifies, but is readily dispersed as small discrete particles in the propellant 12 (or the mixture of propellants 12 and 114). The resulting dispersions are usually stable for at least 30 minutes. This initial dispersion is then mixed with the finely divided disodium cromoglycate. We prefer the finely divided disodium cromoglycate to comprise from 0.1 to 10.0%, and preferably from 1 to 5%, of the initial dispersion. Further propellant 12 and/or propellant 114 (appropriately cooled, e.g. to −50° C.) is then added to the original dispersion or the original dispersion containing the finely divided disodium cromoglycate.

The compositions according to the invention are advantageous in that they give a higher proportion of fine particles in the aerosol cloud produced as compared to equivalent compositions containing propellant 11. A suitable method of determining the proportion of fine particles produced in an aerosol cloud is described in J Pharm. Pharmac. 1973, 25, Suppl. 32P-36P.

The composition is preferably substantially anhydrous. We have found that use of dried disodium cromoglycate in the composition enables freer and easier working of the valve, better dispersion from the valve, and less loss of propellant when the composition has been filled into pressurised packs. We prefer the percentage of water in the formulation expressed as a percentage by weight of the disodium cromoglycate to be less than 2.5 and preferably less than 2.0.

According to a further feature of the invention there is provided disodium cromoglycate having a mass median diameter of less than 20 microns, more preferably in the range 0.01 to 10 microns, and most preferably at least 50% by weight of the particles having a diameter of 2 to 5 microns and containing less than 1% by weight of water.

Such disodium cromoglycate is strongly hygroscopic and is even able to extract water from conventional drying agents such as slightly hydrated silica gel. Very considerable precautions must therefore be taken during its preparation, storage and use to ensure (in so far as is possible) that the disodium cromoglycate does not pick up water from the environment.

'Dry' disodium cromoglycate may be made from disodium cromoglycate containing a larger proportion of water by subjecting such disodium cromoglycate to heat, e.g. to temperatures of from about 110° to 150° C., to a vacuum, to the action of a desiccant, or to a combination of such treatments. In particular we prefer to dry the disodium cromoglycate by subjecting it to a combination of heat and vacuum, a troublesome procedure which provides a strong disincentive to the practical use of the anhydrous material. It is very difficult indeed, without using quite exceptional and expensive techniques, to obtain disodium cromoglycate containing less than about 0.05% by weight of water, and we therefore prefer to use disodium cromoglycate containing more than 0.05% by weight of water.

The finely divided dry disodium cromoglycate may be made by micronising, milling or grinding coarser disodium cromoglycate of appropriate water content. However because of the hygroscopic nature of the disodium cromoglycate, and because of the electrostatic effects associated with mechanical working of the 'dry' material, we prefer to remove the water after the disodium cromoglycate has been reduced to the desired particle size.

The composition may contain other medicaments in addition to the disodium cromoglycate. For example the composition may contain a bronchodilator such as ephidrine, isoprenaline or a suitable salt thereof. The composition preferably contains between about 0.1 and 1.0% by weight of the bronchodilator.

We prefer packages containing from about 8 to 30 ml of composition, e.g. an aerosol pressure pack of 10 ml. The pack preferably has a valve adapted to deliver unit dosages of composition of between 0.025 and 0.25 mls of composition. The container may also contain a ball bearing to assist in the prevention of caking within the container.

The compositions of the invention may be made by mixing the various components at a temperature and pressure at which the propellant is in the liquid phase and the disodium cromoglycate is in the solid phase. The compositions may be filled into aerosol containers using cold, or pressure filling, techniques and appropriate valves, e.g. designed to deliver metered doses of 1, 2 or 4 mg of disodium cromoglycate, are then crimped onto the containers. On operating the valve, the powder will be dispensed in a stream of propellant, which will vaporise providing an aerosol of dry powder. Throughout the preparation of the product care should be exercised to minimise the absorption of moisture. This may be accomplished by operating in a dehumidified atmosphere using only dry materials and equipment. Even with considerable care one expects, even with a non-hygroscopic substance, from about 50 to 100 ppm of moisture to be incorporated in the composition during filling.

A specific and preferred composition comprises a dispersion or suspension of from 0.2 to 2.0% disodium cromoglycate of mass median diameter 0.01 to 10 microns, from 0.15 to 2.0% by weight of a sorbitan or sorbitol ester surfactant and a propellant mixture comprising dichlorodifluoromethane and 1,2-dichloro-1,1,2,2-tetrafluoroethane, the ratio of dichlorodifluoromethane to 1,2-dichloro-1,1,2,2-tetrafluoroethane in said mixture being in the range from 2:1 to 1:1 by weight, the disodium cromoglycate used in the formulation containing from 0.05 to 1% w/w of water and the total formulation containing less than 0.1% w/w of water and having a vapour pressure in the range 35 to 70 pounds per square inch gauge.

The formulations have been found to be stable when stored for 3 months, to have a high $LD_{50}$ in rats and to provide satisfactory dispersions of disodium cromoglycate.

TABLE I

| No. | Micronised disodium cromoglycate | 'Span' 85 | Cetyl Pyridinium Chloride | Soya Lecithin | Sodium Dioctyl Sulphosuccinate | Propellant 11 | Propellant 114 | Propellant 12 | Method of Preparation |
|---|---|---|---|---|---|---|---|---|---|
| 1 | 1.47 | 1.00 | 0.05 | — | — | 10.00 | 13.12 | 74.36 | A |
| 2 | 1.43 | 2.00 | — | — | — | 24.14 | 24.14 | 48.29 | A |
| 3 | 2.86 | 1.50 | 0.08 | — | — | 23.89 | 23.89 | 47.78 | A |
| 4 | 2.93 | 4.00 | — | — | — | 10.00 | 12.46 | 70.61 | A |
| 5 | 5.87 | 2.50 | — | — | — | 10.00 | 12.25 | 69.38 | A |
| 6 | 5.71 | 5.00 | 0.25 | — | — | 22.26 | 22.26 | 44.52 | A |
| 7 | 11.43 | 3.50 | — | — | — | 21.27 | 21.27 | 42.53 | A |
| 8 | 11.73 | 5.00 | 0.25 | — | — | 10.00 | 10.95 | 62.07 | A |
| 9 | 1.43 | — | — | 0.50 | — | 24.52 | 24.52 | 49.03 | A |
| 10 | 2.86 | — | — | 1.00 | — | 24.04 | 24.04 | 48.06 | A |
| 11 | 5.71 | — | — | 2.00 | — | 23.07 | 23.07 | 46.15 | A |
| 12 | 11.43 | — | — | 2.00 | — | 21.64 | 21.64 | 43.29 | A |
| 13 | 1.43 | — | — | — | 0.20 | 24.59 | 24.59 | 49.19 | A |
| 14 | 1.43 | — | — | — | 0.10 | 24.62 | 24.62 | 49.23 | A |
| 15 | 2.86 | — | — | — | 0.40 | 24.19 | 24.19 | 48.36 | A |
| 16 | 2.86 | — | — | — | 0.20 | 24.24 | 24.24 | 48.46 | A |
| 17 | 5.71 | — | — | — | 0.80 | 23.37 | 23.37 | 46.75 | A |
| 18 | 5.71 | — | — | — | 0.40 | 23.47 | 23.47 | 46.95 | A |
| 19 | 11.43 | — | — | — | 1.20 | 21.84 | 21.84 | 43.69 | A |
| 20 | 11.43 | — | — | — | 0.60 | 21.99 | 21.99 | 43.99 | A |
| 21 | 1.44 | — | — | — | 0.20 | — | 39.34 | 59.02 | B |
| 22 | 1.44 | — | — | — | 0.10 | — | 39.38 | 59.08 | B |
| 23 | 2.88 | — | — | — | 0.40 | — | 38.69 | 58.08 | B |
| 24 | 2.88 | — | — | — | 0.20 | — | 38.77 | 58.15 | B |
| 25 | 5.77 | — | — | — | 0.80 | — | 37.37 | 56.06 | B |
| 26 | 5.77 | — | — | — | 0.40 | — | 37.53 | 56.30 | B |
| 27 | 11.54 | — | — | — | 1.20 | — | 34.91 | 52.35 | B |
| 28 | 11.54 | — | — | — | 0.60 | — | 35.15 | 52.71 | B |
| 29 | 2.86 | 4.00 | 0.20 | — | — | 23.24 | 23.24 | 46.46 | A |
| 30 | 11.43 | 5.00 | 0.25 | — | — | 20.83 | 20.83 | 41.66 | A |
| 31 | 5.71 | 5.00 | — | — | — | 22.32 | 22.32 | 44.64 | A |

The compositions of the invention may be used in the treatment of a number of allergic conditions in mammals, e.g. the inhalation treatment of allergic conditions of the airways, such as asthma or allergic rhinitis (hay fever). The treatment is preferably by oral or nasal inhalation and is preferably treatment of man.

Disodium cromoglycate is sometimes known as sodium cromoglycate or cromolyn sodium and is the disodium salt of 1,3-bis(2-carboxychromon-5-yloxy)-propan-2-ol.

The invention is illustrated, but in no way limited by the following Examples in which the parts and percentages are by weight.

EXAMPLE 1

Methods of preparation (a) Dissolve the surface-active agent(s) in the propellant 11 and add the micronised disodium cromoglycate. Disperse by using a high-shear mixer or a homogensier. Cool to −50° C. and add the propellants 114 and 12, also cooled to −50° C. Remix, cold fill into suitable cans, apply valve and crimp.

(b) Cool the propellant 114 to −15° C. and dissolve the surface active agent in it. Add the micronised disodium cromoglycate and mix with a high-shear mixer. Cool to −50° C., add the propellant 12 cooled to −50° C. and remix. Cold fill into suitable cans, apply valves and crimp.

Suitable formulations are shown in Table I in which the figures represent the percentages by weight of the various ingredients.

Compositions 6, 16, 29, 30 and 31 were made up using both dried and undried disodium cromoglycate. When dried disodium cromoglycate was used the percentage of water in the formulation expressed as a percentage by weight of disodium cromoglycate was less than 2. When undried disodium cromoglycate was used the percentage of water, expressed on the same basis, was from 4 to 7.

EXAMPLE 2

(a) Drying of micronised disodium cromoglycate

1. Using heat alone 1 kg of micronised disodium cromoglycate at a moisture content of 5.8% w/w was spread in layers approximately 2 cm thick, and heated for 42 hours at 120° C. After removal from the oven, cooling under conditions preventing ready access to atmospheric moisture, and mixing, the moisture content was 0.35% w/w.

2. Using desiccant alone 10 g of micronised disodium cromoglycate at a moisture content of 6.3% w/w was spread in a thin layer and placed in an enclosed container in which was also placed fresh phosphorous pentoxide, also in a thin layer. After 7 days, the moisture content of the micronised disodium cromoglycate had fallen to 0.13% w/w.

(b) Determination of moisture content of micronised disodium cromoglycate

The water content of disodium cromoglycate may be determined by loss on drying or by Karl-Fischer titration.

(c) Micronising of disodium cromoglycate

By the term 'micronised disodium cromoglycate' we mean that disodium cromoglycate that has been subjected to a process of attrition in a fluid energy mill, for example that manufactured by CHRISPRO LIMITED, 3 ST MARGARET'S STREET, CANTERBURY, KENT, ENGLAND.

EXAMPLE 3

Using the same batch of vials and valves two similar pressurised aerosol formulations were made up using the method set out below. The only difference between the two formulations was that in one disodium cromoglycate containing 0.5% w/w water was used and in the other normal disodium cromoglycate containing 9% w/w water was used.

| Formulation | % w/w |
|---|---|
| Disodium cromoglycate | 2.86 |
| Dioctyl sodium sulphosuccinate | 0.20 |
| Propellant 11 | 24.24 |
| Propellant 114 | 24.24 |
| Propellant 12 | 48.46 |
| | 100.00 |

Method of Preparation

Dissolve the dioctyl sulphosuccinate surface-active agent in the propellant 11 and add the micronised disodium cromoglycate. Disperse by using a high-shear mixer or a homogeniser. Cool to −50° C. and add the propellants 114 and 12, also cooled to −50° C. Remix, cold fill into suitable cans (fill volume 11 ml-fill weight 14 g), apply valves and crimp.

Samples of 15 each of the above cans were stored at 20° C. and after a period of 90 days the average weight loss was determined and expressed in terms of grams loss per year per can. The following results were obtained:

Composition comprising disodium cromoglycate containing 9% w/w water-mean weight loss 0.7664 g/year.

Composition comprising disodium cromoglycate containing 0.5% w/w water-mean weight loss 0.1908 g/year.

These two formulations were also filled into batches of cans fitted either with valves having stems made of a plastics material, or with valves having stems made of metal. The valves were then actuated and the acceptability of the valve action estimated. The following results were obtained:

| | Plastics stem | Metal stem |
|---|---|---|
| Composition comprising disodium cromoglycate containing 0.5% w/w water | Satisfactory | Slow return |
| Composition comprising disodium cromoglycate containing 9% w/w water | Uneven and jerky action | Valve siezes after a few shots |

EXAMPLE 4

Aerosols were produced to the following formulation:
Disodium cromoglycate micronised—1.44% w/w
Sorbitan trioleate—1.00% w/w
Dichlorotetrafluoroethane—39.02% w/w
Dichlorodifluoromethane—58.54% w/w Two lots of aerosols were manufactured using exactly the same method, but one lot using disodium cromoglycate of moisture content 5.0% w/w and the other lot using disodium cromoglycate which had been dried for 16 hours at 120° C. prior to use (moisture content less than 1% w/w). Both lots were filled into identical cans and fitted with identical valves. After storage for one month at 25° C. (ambient humidity) to ensure thorough equilibration of the can contents, the units were examined using a single stage liquid impinger. This apparatus samples the whole cloud delivered from the aerosol applicator and separates it into two fractions by inertial impaction. The fraction of smaller particle size is predominantly smaller than 8 μm and represents material which is likely to be capable of penetration through the human airways and deposition in the lower regions thereof.

The following results were obtained, where each determination shows the percentage by weight of total disodium cromoglycate from 20 actuations of the aerosol recovered from each location:

| Moisture content of disodium cromoglycate used | 5.0% w/w | | less than 1% w/w | |
|---|---|---|---|---|
| Recovered from applicator | 8.1 | 10.1 | 10.3 | 13.5 |
| Recovered from greater than 8 μm fraction | 72.2 | 71.0 | 57.3 | 55.5 |
| Recovered from less than 8 μm fraction | 19.7 | 18.9 | 32.4 | 31.0 |

Moisture contents, when determined within 2 days of manufacture, were 1040 and 1220 μg.g$^{-1}$ for the 'wet' formulation and 270 and 340 μg.g$^{-1}$ for the 'dry' formulation.

EXAMPLE 5

Method

The sorbitan ester is dispersed in up to half the propellant 12 at −40° C. while stirring with a high dispersion mixer. The dry disodium cromoglycate is added to the resulting dispersion and disperses in it very readily. The balance of the propellant 12 is then added at −50° C., followed by the propellant 114 also cooled to −50° C. The resulting mixtures are then filled into vials onto which valves, e.g. metering valves, are subsequently crimped.

| Ingredients | % w/w | % w/w |
|---|---|---|
| Dried micronised disodium cromoglycate | 0.3605 | 1.4420 |
| Sorbitan trioleate | 0.2500 | 1.0000 |
| Propellant 114 | 39.7558 | 39.0232 |
| Propellant 12 | 59.6337 | 58.5348 |

Stability

Batches of vials fitted with metering valves and containing the above formulations were stored at 5° C., 25° C. and 37° C. respectively for a period of 12 months.

Two further batches of vials were stored at respectively (a) temperatures which varied from 15° C. to 37° C., and (b) at a temperature of 45° C. for a period of 6 months. No change in (a) the amount of disodium cromoglycate dispensed per shot, (b) the content of fine particles in the cloud or (c) the crystal size of the disodium cromoglycate was observed over the period of observation.

EXAMPLE 6

A number of pressurised drug formulations some containing propellant 11 and some not containing propellant 11 were made up and tested using the method and apparatus described by Bell J.H., Brown K. and Glasby J. in J Pharm Pharmac, 25, Suppl. 32P-36P (1973). The multistage liquid impinger used in the present experiments was however modified to give cut off stages at 6.9 $\mu$m and 3.8 $\mu$m.

The composition of the formulations, on a weight % basis, and the results of the tests are shown in the following tables:

TABLE A

| FORMULATION | A | B | C |
|---|---|---|---|
| Drug, micronised, dried | 1.4663 | 1.4286 | 1.4420 |
| Sorbitan trioleate | 1.0000 | 2.0000 | 1.0000 |
| Cetyl pyridinium chloride | 0.0500 | — | — |
| Propellant 11 | 10.0000 | 24.1429 | — |
| Propellant 114 | 13.1226 | 24.1429 | 39.0232 |
| Propellant 12 | 74.3611 | 48.2856 | 58.5348 |
| Weight percent of cloud smaller than | | | |
| (i) 6.9 $\mu$m | 11.4 | 14.9 | 29.2 |
| (ii) 3.8 $\mu$m | 8.4 | 7.4 | 13.7 |

TABLE B

| FORMULATION | D | E | F | G |
|---|---|---|---|---|
| Drug, micronised | 0.7148 | 0.7210 | 0.1430 | 0.1442 |
| Sorbitan trioleate | 0.5000 | 0.25000 | 0.2000 | 0.0500 |
| Propellant 11 | 39.5141 | — | 39.8628 | — |
| Propellant 114 | — | 39.6116 | — | 39.9223 |
| Propellant 12 | 59.2711 | 59.4174 | 59.7942 | 59.8835 |
| Weight percent of cloud smaller than | | | | |
| (i) 6.9 $\mu$m | 25.4 | 45.4 | 29.9 | 57.9 |
| (ii) 3.8 $\mu$m | 11.8 | 33.0 | 16.5 | 41.0 |

The results in these Tables show a two to threefold advantage for the formulations which do not contain propellant 11.

I claim:

1. A method of treatment of asthma which comprises administration to an asthmatic patient of an effective amount of an inhalation composition comprising a dispersion or suspension of from 0.2 to 2.0% of disodium cromoglycate of mass median diameter 0.01 to 10 microns, from 0.15 to 2.0% by weight of a sorbitan or sorbitol ester surfactant and a propellant mixture comprising dichlorodifluoromethane and 1,2-dichloro-1,1,2,2-tetrafluoroethane and containing substantially no trichloromonofluoromethane, the ratio of dichlorodifluoromethane to 1,2-dichloro-1,1,2,2-tetrafluoroethane in said mixture being in the range from 2:1 to 1:1 by weight, the disodium cromoglycate used in the formulation containing from 0.05 to 1% w/w of water and the total formulation containing less than 0.1% w/w of water and having a vapour pressure in the range 35 to 70 pounds per square inch gauge.

2. A method according to claim 1, wherein at least 50% by weight of the particles of disodium cromoglycate have a diameter of 2 to 5 microns and containing from 0.2 to 1.2% by weight of surfactant.

3. An inhalation composition comprising a dispersion or suspension of from 0.2 to 2.0% disodium cromoglycate of mass median diameter 0.01 to 10 microns, from 0.15 to 2.0% by weight of a sorbitan or sorbitol ester surfactant and a propellant mixture consisting essentially of dichlorodifluoromethane and 1,2-dichloro-1,1,2,2-tetrafluoroethane, the ratio of dichlorodifluoromethane to 1,2-dichloro-1,1,2,2-tetrafluoroethane in said mixture being in the range from 2:1 to 1:1 by weight, the disodium cromoglycate used in the formulation containing from 0.05 to 1% w/w of water and the total formulation containing less than 0.1% w/w of water and having a vapour pressure in the range 35 to 70 pounds per square inch gauge.

* * * * *

UNITED STATES PATENT AND TRADEMARK OFFICE
CERTIFICATE OF CORRECTION

PATENT NO. : 4,405,598

DATED : September 20, 1983

INVENTOR(S) : KENNETH BROWN

It is certified that error appears in the above-identified patent and that said Letters Patent is hereby corrected as shown below:

Cover page, please insert the following

--Foreign Application Priority Data

| Jan. 30, 1976 | (U.K.) | ....... | 3672/76 |
| Dec. 8, 1976 | (U.K.) | ....... | 51136/76 |
| Jan. 19, 1977 | (U.K.) | ....... | 2015/77 |
| July 19, 1977 | (U.K.) | ....... | 30169/77 -- |

Signed and Sealed this

Fourteenth Day of April, 1987

Attest:

DONALD J. QUIGG

Attesting Officer

Commissioner of Patents and Trademarks